United States Patent [19]

Shimizu et al.

[11] Patent Number: 5,237,068
[45] Date of Patent: Aug. 17, 1993

[54] PROCESS FOR PRODUCING PYRIDINE BASES

[75] Inventors: Shinkichi Shimizu, Hirakata; Nobuyuki Abe, Ikoma; Masanori Doba, Osaka; Akira Iguchi, Kameoka, all of Japan

[73] Assignee: Koei Chemical Company, Limited, Osaka, Japan

[21] Appl. No.: 742,585

[22] Filed: Aug. 7, 1991

Related U.S. Application Data

[63] Continuation of Ser. No. 475,865, Feb. 6, 1990, abandoned.

[30] Foreign Application Priority Data

Feb. 8, 1989 [JP] Japan ................................. 01-29497

[51] Int. Cl.$^5$ .................. C07D 213/09; C07D 213/10
[52] U.S. Cl. ...................................... 546/251; 546/250
[58] Field of Search ................................. 546/250, 251

[56] References Cited

U.S. PATENT DOCUMENTS

| | | | |
|---|---|---|---|
| 4,220,783 | 9/1980 | Chang et al. | 546/251 |
| 4,675,410 | 6/1987 | Feitler et al. | 546/251 |
| 4,810,794 | 3/1989 | Shimizu et al. | 546/251 |
| 4,861,894 | 8/1989 | Bowes et al. | 546/251 |
| 4,866,179 | 9/1989 | Cheng et al. | 546/251 |
| 4,960,894 | 10/1990 | Hoelderich et al. | 546/250 |

FOREIGN PATENT DOCUMENTS

| | | | |
|---|---|---|---|
| 0131887 | 7/1984 | European Pat. Off. | 546/251 |
| 0232182 | 2/1987 | European Pat. Off. | 546/251 |
| 0263464 | 10/1987 | European Pat. Off. | 546/251 |
| 0318845 | 11/1988 | European Pat. Off. | 546/251 |
| 1-009974 | 1/1989 | Japan | 546/251 |
| 649974 | 1/1989 | Japan | 546/251 |
| 6490171 | 4/1989 | Japan | 546/251 |

OTHER PUBLICATIONS

L. G. Wade, Jr. "Organic Chemistry" Index Page, Prentice Hall Pub. 1987.

*Primary Examiner*—Alan L. Rotman
*Attorney, Agent, or Firm*—Stevens, Davis, Miller & Mosher

[57] ABSTRACT

The present invention provides a process for producing pyridine bases which comprises reacting an aliphatic aldehyde and/or a ketone with ammonia in the presence of a catalyst in gaseous phase, said catalyst comprising a zeolite containing (a) an element belonging to the platinum group and (b) at least one element selected from the group consisting of the elements of Groups IIB, IIIA and IVA of the periodic table and the having an atomic ratio of Si to elements consisting of Al, B, Fe and/or Ga of about 12 to about 1,000 and a constraint indedx of about 0.8 to about 12.

7 Claims, No Drawings

PROCESS FOR PRODUCING PYRIDINE BASES

This application is a continuation of application Ser. No. 07/475,865, filed Feb. 6, 1990, now abandoned.

The present invention relates to a process for producing pyridine bases by reacting an aliphatic aldehyde and/or a ketone with ammonia in gaseous phase by the use of a specified zeolite catalyst, and particularly preferably, to a process for producing pyridine and picolines by reacting acetaldehyde and formaldehyde with ammonia in gaseous phase.

It is known that crystalline aluminosilicate, or the so-called zeolite, is used as a catalyst for producing pyridine bases from aliphatic aldehyde and/or ketone and ammonia (U.S. Pat. No. 4,220,783; Japanese Patent Application Kokai (Laid-Open) No. 60-38362).

U.S. Pat. No. 4,200,783 discloses that pyridine was obtained in a yield of 40% or below by using an H+-form ZSM-5 or a ZSM-5 ion-exchanged with cadmium, copper or nickel; and European Patent Application No. 131,887 discloses that, in the case of fixed bed catalyst, pyridine and β-picoline were obtained from acetaldehyde, formaldehyde and ammonia in a total yield of 57.9%, based on the total carbon number of acetaldehyde and formaldehyde, by the use of a catalyst composed of H+ form Silicalite S-115, and the yield of pyridine economically more expensive than β-picoline was 45.5%. In the case of fluidized bed catalyst more excellent than fixed bed catalyst as a mode of reaction, total yield of pyridine and β-picoline was 78.5%, and the yield of pyridine was 51.7%, by the use of the same catalyst as above.

By-product of this reaction includes a polymeric compound having pyridine ring. It has a strong basicity, and is strongly adsorbed and accumulated onto zeolite catalyst, or the so-called deposition of carbon onto zeolite catalyst takes place, due to which the catalytic activity is deteriorated. Accordingly, the catalyst must be periodically regenerated by aeration for the sake of reactivation. However, the prior zeolite catalysts have been disadvantageous in that their catalytic activity becomes lower when the cycle of reaction-regeneration has not yet been repeated many times.

It is the object of the present invention to provide a process for producing pyridine bases using a specified zeolite catalyst.

The present inventors earnestly searched for a catalyst with which pyridine bases can be obtained with a high efficiency and with only a small decrease in catalytic activity after repetition of reaction-regeneration cycle. As a result, there was discovered a surprising fact that a catalyst prepared by incorporating (a) an element belonging to the platinum group and (b) at least one element selected from the group consisting of Groups IIB, IIIA and IVA of the periodic table and the iron family elements, except for iron, into a zeolite having an atomic ratio of Si to metals consisting of Al, B, Fe and/or Ga of about 12 to about 1,000 and a constraint index of about 0.8 to about 12 is small in the decrease of catalytic activity after repeated reaction-regeneration cycle and can achieve a high yield of pyridine bases. Based on this discovery, the present invention was accomplished.

Thus, the present invention relates to a process for producing pyridine bases which comprises reacting an aliphatic aldehyde and/or a ketone with ammonia in gaseous phase in the presence of a catalyst, said catalyst comprising a zeolite containing (a) an element of the platinum group and (b) at least one element selected from the group consisting of the elements of Groups IIB, IIIA and IVA of the periodic table and the iron family elements, except for iron (hereinafter, these elements are generically referred to as "second element"), and said zeolite having an atomic ratio of Si to elements consisting of Al, B, Fe and/or Ga of about 12 to about 1,000 and a constraint index of about 0.8 to about 12.

The invention will be illustrated more concretely. Examples of the aliphatic aldehydes used in the present invention include those having 1 to 5 carbon atoms such as formaldehyde, acetaldehyde, propionaldehyde, butyraldehyde, acrolein, methacrolein, crotonaldehyde and the like. Examples of the aliphatic ketone include those having 3 to 5 carbon atoms such as acetone, methyl ethyl ketone, methyl vinyl ketone, diethyl ketone and the like. Depending on the combination of starting aliphatic aldehyde and/or aliphatic ketone, the main compound constituting the produced pyridine bases is determined. Typical examples of this relationship is shown in Table 1.

TABLE 1

| Aldehyde, ketone | Main product |
| --- | --- |
| Acetaldehyde | α-Picoline, γ-picoline |
| Acetaldehyde + formaldehyde | Pyridine, β-Picoline |
| Acrolein + acetaldehyde | Pyridine |
| Acrolein + propionaldehyde | β-Picoline |
| Propionaldehyde + formaldehyde | 3,5-Lutidine |
| Crotonaldehyde + acetone | 2,4-Lutidine |
| Acetone + formaldehyde | 2,6-Lutidine |
| Acetone | 2,4,6-Collidine |

When, in the zeolite of the invention, the atomic ratio of Si to Al, B, Fe and/or Ga is about 12 to about 1,000, particularly preferably about 15 to 500, and the constraint index is about 0.8 to about 12, the catalyst prepared with the zeolite exhibits high performances.

As used herein, the term "Constraint index" expresses pore characteristics of catalyst defined by Frillette et al. (Journal of Catalysis, 67, 218–222 (1981)). Although this value shows some deviations depending on the method of measurement, the results of the measurement by Frillette et al. are shown in Table 2.

TABLE 2

| Zeolite and others | Constraint index |
| --- | --- |
| Amorphous silica-alumina | 0.6 |
| REY | 0.4 |
| Mordenite (Y Zeolon) | 0.4 |
| Silicalite S-115 | ~1 |
| ZSM-12 | 2 |
| Erionite | 3.8 |
| ZSM-35 | 4.5 |
| ZSM-5 | 8.3 |
| ZSM-11 | 8.7 |
| ZSM-23 | 9.3 |

Examples of the zeolite used in the invention include various zeolites including aluminosilicates such as ZSM-type zeolites and Silicalite S-115; heterosilicates such as borosilicate, iron-silicate and gallium-silicate; etc. These zeolites are readily available commercially or are prepared according to known methods. For example, ZSM-type zeolites are available from MOBILE CATALYST CORPORATION OF JAPAN, and their production processes are detailed in U.S. Pat. Nos. 3,702,886 (ZSM-5), 3,709,979 (ZSM-11), 3,832,449 (ZSM-12), and 4,016,245 (ZSM-35). Silicalite S-115 is commercialized by Union Carbide Corp. and is detailed in U.S. Pat. No. 4,061,724. Borosilicate can easily be synthesized according to the method detailed in U.S. Pat. No. 4,292,458 (Standard Oil Company (Indiana)). Iron- and gallium-silicates can easily be synthesized according to the method detailed by Inui et al. (Yuki Gosei Kagaku Kyokai-shi, 44, 60–70 (1986)).

As a zeolite used in invention, any of alkali (sodium, potassium and the like) ion form, ammonium ion form and proton form may be used, among which ammonium ion form of zeolite is most preferable. Accordingly, alkali ion form or proton form of zeolite is preferably converted to ammonium ion form previously by several times repeating a procedure of dipping it in an aqueous solution of ammonium salt such as ammonium chloride, ammonium nitrate, ammonim acetate or the like and then filtering it.

As an element of the platinum group, platinum, palladium, rhodium and ruthenium are preferable, and they may be used either alone or in combination of two or more. Although the platinum group element may be incorporated into a zeolite in any form, it is usually incorporated in the form of ions having a platinum group element such as metallic ion and complex ion, or a compound of a platinum group element such as an oxide, halide, halogenoacid, halogenosalt, complex, chelate or organometallic compound. They may be used either alone or in combination of two or more.

Although the platinum group metal may be incorporated by any method, it is usually incorporated into a zeolite or a zeolite previously containing a second element by ion-exchange method, kneading method impregnation method, immersion method, precipitation method or evaporation to dryness.

A method for incorporating platinum group element will be concretely explained by referring to a case of using a zeolite into which incorporation of a second element is not practised previously. (1) In ion exchange method, a zeolite of the above-mentioned alkali ion form, ammonium ion form or proton form, preferably ammonium ion form, is dipped in a solution of ions containing a necessary quantity of a platinum group element, and the mixture is stirred at a predetermined temperature. The zeolite thus ion-exchanged is filtered out and washed with water. Then, the ion-exchanged zeolite is dried usually at a temperature of 100°–200° C., and it is calcined if desired. As ions having a platinum group element used in the invention, ammine complex ions are particularly preferable. (2) In the kneading method, a compound of a platinum group element is mixed or kneaded with proton form or ammonium ion form of zeolite either in the state of powder or together with water. Then the mixture thus obtained is dried, and thereafter calcined if desired. (3) In the immersion method, proton form or ammonium ion form of zeolite is immersed in an aqueous solution of a compound of a platinum group element. Then, the immersed zeolite is recovered by filtration, dried, and if desired it is calcined. (4) In the impregnation method, an aqueous solution of a compound of platinum group element is impregnated into proton form or ammonium ion form of zeolite. Then, the impregnated zeolite is dried, and if desired it is calcined. (5) In the method of evaporation to dryness, a proton form or ammonium ion form of zeolite is added to an aqueous solution of a compound of a platinum group element and the mixture is evaporated to dryness, and if desired it is calcined. However, the present invention is not limited by these methods.

Although preferable content of the platinum group element varies depending on the kind of zeolite and the kind and form of platinum group element, it is about 0.0001 to about 0.5% by weight based on zeolite.

Examples of the second element include zinc, cadmium, thallium, tin, lead, cobalt and the like, among which thallium, lead and cobalt are preferable. These elements may be incorporated either alone or in combination of two or more. Although the second element may be incorporated into zeolite in any form, it is usually incorporated in the form of metallic ion, oxide, halide, sulfate, phosphate, nitrate, hydroxide, sulfide, silicate, titanate, borate, carbonate, organic carboxylate, chelate, organometallic compound or the like, either alone or in combination of two or more. Although the second element may be incorporated by any methods, usually it is incorporated into a zeolite or a zeolite into which a platinum group element has previously been incorporated by ion exchange method, kneading method impregnation method, precipitation method or the method of evaporation to dryness.

Referring to the case of using a zeolite into which platinum group element has not been incorporated previously, examples of the method for incorporating the second element will be mentioned below more concretely. Thus, according to the ion exchange method (1), alkali ion form, ammonium ion form or proton form of zeolite, preferably ammonium ion form of zeolite, is dipped into an aqueous solution containing 0.01–2 gram ion/liter of chloride, nitrate, acetate or the like of the second element, and the mixture is stirred at a predetermined temperature and filtered. After repeating such dipping, stirring and filtering. After repeating such dipping, stirring and filtering, finally the ion-exchanged zeolite is washed with water. Then, the ion-exchanged zeolite is dried usually at 100°–200° C., and if desired it is calcined. (2) In the kneading method, a compound of the second element is mixed or kneaded in the form of powder itself or together with water or the like with alkali ion form, ammonium ion form or proton form of zeolite and then, the mixture is dried and, if desired, calcined. Otherwise, a hydroxide of a second element is prepared by neutralizing its metallic compound such as nitrate, acetate or the like with aqueous ammonia or the like, and it is kneaded together with alkali ion form, ammonium ion form or proton form of zeolite, and the mixture is dried and calcined if desired. (3) In the immersion method, alkali ion form, ammonium ion form or proton form of zeolite, preferably ammonium ion form of nitrate or acetate of a second element, and then the mixture is dried, and if desired it is calcined. (4) In precipitation method, alkali ion form, ammonium ion form or H+ form of zeolite is dispersed into an aqueous solution of a compound of a second element such as nitrate, acetate or the like, and aqueous ammonia is added thereto, whereby hydroxide or the like is precipitated onto the surface of the zeolite, after which the zeolite containing such precipitate is washed with water, dried and if desired it is calcined. (5) In the method of evaporation to dryness, alkali ion form, ammonium ion form or proton form of zeolite is added to an aqueous solution of a compound of a second element, and the mixture evaporated to dryness, and it is calcined if desired. However, the invention is not limited by these methods.

The incorporation of the second element may be carried out either before incorporation of the platinum group element, or after it, or simultaneously with it.

Although the quantity of the second element to be incorporated into zeolite varies depending on the kind of zeolite and the kind and form of the second element, it is about 0.005–about 1.0 mg equivalent/gram zeolite.

The calcination is carried out usually in the atmospheric air or in other gases such as nitrogen, carbon dioxide and the like at a temperature of 350°–800° C. for a period of several hours. However, calcination of catalyst is not always necessary, because the catalyst is heated in a reactor.

The zeolite containing the platinum group element and second element is molded into a cylindrical or columnar form either directly or after mixing with silica, diatomaceous earth, kaolin, bentonite, alumina and/or silica-alumina, by means of a tableting machine. Otherwise, it is kneaded together with water, polyvinyl alcohol or vinyl acetate, and then molded by extrusion. The molded products can be used as a catalyst for a fixed bed. The zeolite containing the platinum group element and second element is mixed with silica, diatomaceous earth, kaolin, bentonite, alumina and/or silica-alumina and water to make a slurry, and the slurry is spray-dried to obtain spherical microbeads which can be used as a catalyst for fluidized bed. Otherwise, into a zeolite previously molded together with silica, diatomaceous earth, kaolin, bentonite, alumina and/or silica-alumina may be incorporated a platinum group element and a second element by the above-mentioned methods except by kneading to obtain the molded product as the catalyst of the present invention. In any of these methods, the molded product may be calcined in air or other gases such as nitrogen, carbon dioxide and the like at 350°–800° C. for several hours to give a sufficient strength to the molded product and to remove the volatile components present in binder, etc. However, calcination of the catalyst is not always necessary, because the catalyst is heated in a reactor.

The reaction of the present invention is carried out in fixed bed, fluidized bed or moving bed.

Molar ratio of ammonia to the aliphatic aldehyde and/or ketone is about 0.5 to about 5 moles/mole. Space velocity (SV) is 100 to 10,000 hr$^{-1}$ and preferably 300 to 3,000 hr$^{-1}$. The reaction temperature is preferably 350° to 600° C. Although pressure of the reacting gases may range from a pressure lower than the atmospheric pressure to a pressure of several atmospheres, a pressure of atmospheric pressure to about 2 atmospheres is convenient.

A combination of aliphatic aldehydes or ketones particularly desirable for the synthesis of pyridine or $\beta$-picoline is a combination of acetaldehyde and formaldehyde, and molar ratio acetaldehyde: formaldehyde:ammonia is adjusted to 1:0.3–3:0.5–5. Particularly, when the catalyst of the invention is used, pyridine which is economically more expensive than $\beta$-picoline is preferentially produced. For obtaining $\beta$-picoline or $\gamma$-picoline, the use of acetaldehyde only as a combination of aldehyde and ketone is preferable. The starting gas may contain water, methanol or the acetaldehyde and formaldehyde are used as starting materials, however, quantity of methanol should preferably be 0.5 mole or below per one mole of acetaldehyde. Formaldehyde may be fed in the form of formalin. Dimer, trimer, other oligomers and polymers of aliphatic aldehyde and ketone capable of generating monomeric aldehyde or ketone in the evaporator or reactor may also be used as the aliphatic aldehyde or ketone.

Since the catalyst contains a platinum group metal and the second elements, combustion of the carbon deposited on the catalyst is promoted, which makes the regeneration of catalyst smoother and more perfect than zeolite catalysts known in the art, and pyridine bases can be obtained in a high yield. Regeneration of the catalyst is carried out according to the hitherto known procedure. That is, air is passed through the catalyst layer at a high temperature not exceeding the heat resistant temperature of the catalyst, preferably 350°–800° C., to burn the carbon deposited on the catalyst. If desired, the air may be diluted with steam, nitrogen, carbon dioxide or the like.

When the catalyst of the invention is used, the yield of pyridine is 65% and the total yield of pyridine and picoline is 83% based on the total carbon number of starting aldehyde and ketone, in the early stage. After 50 times repeating the reaction-regeneration cycle, the yield of pyridine is 61% and the total yield of pyridine and picoline is 80% (Example 1). On the other hand, in Comparative Example 2 using a catalyst containing no platinum group element, the yield of pyridine is 63% and total yield of pyridine and picoline is 81% in the early stage, and the yield of pyridine is 55% and total yield of pyridine and picoline is 74% after 30 times repeating the reaction-regeneration cycle. In other words, in Comparative Example 2, the catalytic activity shows a larger decrease at a considerably smaller number of repetition of reaction-regeneration cycle than in Example 1. Accordingly, the catalyst of the present invention can be regenerated more satisfactorily and is much smaller in the decrease of catalytic performances as compared with a catalyst containing no platinum group element, and it can give economically more expensive pyridine in a high yield.

The present invention will be illustrated in more detail with reference to the following examples. The invention is by no means limited by these examples.

In the examples, results of the reaction are based on total carbon atom number of starting aliphatic aldehyde and ketone, and they were calculated according to the following formulas:

$$\text{Yield of pyridine (\%)} = \frac{\text{Total carbon atom number of produced pyridine}}{\text{Total carbon atom number of starting aldehyde and ketone}} \times 100$$

$$\text{Yield of } \alpha\text{-, } \beta\text{- and } \gamma\text{-picolines (\%)} = \frac{\text{Total caron atom number of produced } \alpha\text{-, } \beta\text{- and } \gamma\text{-picolines}}{\text{Total carbon atom number of starting aldehyde and ketone}} \times 100$$

EXAMPLE 1

According to the method of Yashima (Shokubai, 23 (3), 232 (1981)), ZSM-5 zeolite was synthesized in the following manner.

Thus, solution A was prepared by mixing together 433.4 g of distilled water, 4.6 g of aluminum sulfate, 55.8 g of tetra-n-propylammonium bromide and 40 g of sulfuric acid. Solution B was prepared by mixing 320 g of distilled water and 453 g of sodium silicate No. 3. Solution C was prepared by mixing 754 g of distilled water and 189 g of sodium chloride. The solution C was charged into a stainless steel autoclave having 3 liters of volume. While vigorously stirring it, the solutions A and B were dropwise added thereto, while controlling pH of the mixture so as to keep in the range of 9.5–11. The autoclave was tightly closed, heated to 160° C. and continuously stirred, and in this state a hydrothermal synthesis was carried out for 20 hours. In this period, the gauge pressure was 5–6 kg/cm$^2$. After completion of the reaction, the product was cooled to room temperature, and collected by filtration. After repeating washing and filtration until chlorine ion concentration in the filtrate reached ppm or below, the product was dried at 110° C. for 16 hours and calcined in air at 530° C. for 4 hours to obtain 112 g of Na$^+$, form of ZSM-5 as a white crystalline substance. The X ray diffraction spectrum of this white crystal coincided with that of ZSM-5 mentioned in Japanese Patent Publication No. 46-10064. Analyses revealed that its Si/Al atomic ratio was equal to 90.

After 3 times subjecting the Na$^+$ form of ZSM-5 zeolite thus obtained to ion exchange with each one liter portion of 5% aqueous solution of ammonium chloride at 50°–60° C. for one hour. Then, the ZSM-5 ion-exchanged with NH$_4^+$ was filtered off, repeatedly washed with water and filtered until chlorine ion concentration of the filtrate reached 1 ppm or below, and then dried at 110° C. for 16 hours to obtain 106 g of NH$_4^+$ form of ZSM-5 zeolite, as a crystalline product.

Twenty grams of this NH$_4^+$ form ZSM-5 was subjected to ion-exchange with 200 ml of 0.1M aqueous solution of thallium nitrate at 80° C. for 2 hours. Then, the product thus obtained was filtered off, washed with 20 times its quantity of distilled water in several portions, dried at 110° C. for 16 hours to obtain Tl$^+$ form of ZSM-5. This zeolite was impregnated with an aqueous solution containing palladium ammine complex nitrate, after which the mixture was dried at 110° C. for 16 hours and calcined in air at 530° C. for 4 hours to obtain a catalyst having Tl content of 3.0% and Pd content of 0.01%.

Three grams of this catalyst was packed into a glass tubular reactor having an inner diameter of 12.6 mm. A mixture of 2 moles of acetaldehyde and 1 mole of formaldehyde (40% aqueous solution) was vaporized, mixed with 4 moles of preheated ammonia gas, and the resulting gaseous mixture passed through the reactor kept at 450° C. at a SV of 1,000 hr$^{-1}$. The reaction product was absorbed into water and analyzed by a FID gas chromatography. The results averaged over 3 hours from the start of reaction were as follows: (yields) pyridine 65%, α-picoline 6%, β-picoline 10%, γ-picoline 3%, total yield 84%. Then, the catalyst was regenerated by the method of aeration. Thereafter, such reaction-regeneration cycle was repeated 49 times. The results of the 50th reaction are given below: (yields) pyridine 61%, a-picoline 6%, β-picoline 10%, γ-picoline 3%, total yield 80%.

EXAMPLE 2

Zn$^{++}$ form of ZSM-5 was prepared by the same procedure as in Example 1, except that the thallium nitrate was replaced by zinc nitrate. Then, it was kneaded together with ruthenium chloride and water. The obtained mixture was dried at 110° C. for 16 hours, and calcined in air at 530° C. for 4 hours to obtain a catalyst having Zn content of 0.7% and Ru content of 0.01%.

Using this catalyst, a reaction was carried out in the same manner as in Example 1 to obtain the results shown in Table 1.

EXAMPLE 3

A catalyst having Cd content of 0.5% and Pd content of 0.01% was prepared by the same procedure as in Example 1, except that the thallium nitrate was replaced by cadmium nitrate.

Using this catalyst, a reaction was carried out in the same manner as in Example 1 to obtain the results shown in Table 1.

EXAMPLE 4

Pb$^{++}$ form of Silicalite molded material (alumina binder) was prepared by the same procedure as in Example 1, except that the Na$^+$ form of ZSM-5 and the thallium nitrate were replaced by Silicalite molded material (alumina binder) manufactured by UCC and lead nitrate, respectively. Then, it was immersed in an aqueous solution of platinum ammine complex nitrate, and the mixture was dried at 110° C. for 16 hours, and calcined in air at 530° C. for 4 hours to obtain a catalyst having Pb content of 2.6% and Pt content of 0.01%.

Using this catalyst, a reaction was carried out in the same manner as in Example 1 to obtain the results shown in Table 1.

EXAMPLE 5

A crystalline iron silicate zeolite was synthesized in the following manner.

Thus, solution A was prepared by dissolving 34 g of Fe(NO$_3$)$_3$ 9H$_2$O and 34 g of tetra-n-propylammonium chloride in 150 g of distilled water. Solution B was prepared by suspending 70 g of fumed silica in 700 g of distilled water. Solution C was prepared by dissolving 7.4 g of sodium hydroxide in 50 g of distilled water. The solutions A and B were added to the solution C, and the mixture was heated and stirred in an autoclave at 160° C. for 60 hours. In this period, pH of the reaction mixture changed from 12.4 to 11.4. The solid product thus produced was washed with water until pH of the filtrate reached 7.3, and there was obtained 72.7 g of Na$^+$ form of iron silicate zeolite of a white crystalline product. X ray diffraction analysis revealed that this product had a crystal structure of ZSM-5.

The Na$^+$ form of iron silicate zeolite thus obtained was three times subjected to ion-exchange with 5% aqueous solution of ammonium chloride at 50°–60° C. for one hour, after which the zeolite ion-exchanged with NH$_4^+$ was washed with water until chlorine ion concentration in the washing reached 1 ppm or below, and dried at 110° C. for 16 hours to obtain an NH$_4^+$ form of iron silicate zeolite. Then, this zeolite was impregnated in an aqueous solution containing platinum ammine complex nitrate and the mixture was dried at 110° C. for 16 hours to obtain a zeolite containing platinum element. On the other hand, aqueous ammonia was added to an aqueous solution of lead nitrate for neutralization and the resulting precipitate was washed with water to obtain a pasty lead hydroxide. After uniformly kneading this hydroxide with the zeolite containing platinum element in a mortar, the mixture was dried at 110° C. for 14 hours and calcinated in air at 530° C. for 4 hours to prepare a catalyst having Pt content of 0.01% and PbO content of 2.9%.

Using this catalyst, a reaction was carried out in the same manner as in Example 1 to obtain the results shown in Table 1.

EXAMPLE 6

A $Na^+$ form of gallium silicate zeolite having a crystal structure of ZSM-5 was produced by the same procedure as in Example 5, except that the $Fe(NO_3)_3 9H_2O$ was replaced by 1.87 g of $Ga(NO_3)_3.xH_2O$. After subjecting it to ion-exchange to form $NH_4^+$ form of gallium silicate zeolite, it was immersed in an aqueous solution of cobalt nitrate and the mixture was dried at 110° C. for 16 hours. Then, it was impregnated with an aqueous solution of platinum ammine complex nitrate, dried at 110° C. for 16 hours and calcined in air at 530° C. for 4 hours to obtain a zeolite containing platinum element. Then, it was kneaded together with kaolin and water in a mortar (zeolite/kaolin=70/30), and the mixture was molded, dried at 110° C. for 16 hours, and calcined in air at 530° C. for 4 hours to obtain a catalyst having CoO content of 0.7% and Pt content of 0.01%.

Using this catalyst, a reaction was carried out in the same manner as in Example 1 to obtain the results shown in Table 1.

EXAMPLE 7

A crystalline boroaluminosilicate zeolite was synthesized in the following manner.

Thus, solution A was prepared by dissolving 2.00 g of aluminum sulfate, 34 g of tetra-n-propylammonium chloride and 0.4 g of boric acid in 150 g of distilled water. Solution B was prepared by suspending 70 g of fumed silica in 700 g of distilled water. Solution C was prepared by dissolving 8.0 g of sodium hydroxide in 50 g of distilled water. The solutions A and B were added to the solution C, and the mixture was heated and stirred in an autoclave at 180° C. for 48 hours. In this period, pH of the reaction mixture changed from 12.0 to 11.0. The solid product thus obtained was washed with water until pH of the filtrate reached 7.3, and there was obtained 70.0 g of an $Na^+$ form boroaliminosilicate zeolite of a white crystalline product. X ray diffraction analysis revealed that this product had a crystal structure of ZSM-5.

The $Na^+$ form boroaluminosilicate zeolite thus obtained was three times subjected to ion-exchange with 5% aqueous solution of ammonium chloride at 50°-60° C. for one hour, and then, the zeolite ion-exchanged with $NH_4^+$ was washed with water until chlorine ion concentration in the filtrate reached 1 ppm or below and dried at 110° C. for 16 hours to obtain an $NH_4^+$ form of boroaluminosilicate zeolite. Then, a catalyst was prepared by the same procedure as in Example 1, except that the $NH_4^+$ form of ZSM-5 zeolite, the zinc nitrate and the ruthenium chloride were replaced by the $NH_4^+$ form of boroaluminosilicate zeolite, cobalt nitrate and rhodium chloride, respectively. The catalyst had Co content of 0.1% and Rh content of 0.01%.

Using this catalyst, a reaction was carried out in the same manner as in Example 1 to obtain the results shown in Table 1.

EXAMPLE 8

ZSM-11 zeolite was synthesized under the following conditions according to the procedure mentioned in Example 5 of Japanese Patent Application Kokai (Laid-Open) No. 54-52699. Thus, as a silica source, sodium silicate was used. As a source of alumina, aluminum sulfate was used. As a template, heptamethylenediamine was used. A mixture of these materials was stirred at 160° C. for 10 days for the sake of crystallization. Composition of the product was as follows: $SiO_2/Al_2O_3=90$, $H_2O/SiO_2=40$, $Na/SiO_2=0.59$, diamine/$SiO_2=0.02$. The product was washed with water, dried and calcined in air in the usual manner. X ray diffraction analysis revealed that it was ZSM-11 zeolite.

The $Na^+$ form of ZSM-11 zeolite thus obtained was three times subjected to ion-exchange with 5% aqueous solution of ammonium chloride at 50°-60° C. for one hour, and then, the ZSM-11 ion-exchanged with $NH_4^+$ was washed water until chlorine ion concentration in the filtrate reached 1 ppm or below and dried at 110° C. for 16 hours to obtain an $NH_4^+$ form of ZSM-11 zeolite. On the other hand, an aqueous solution of thallium nitrate was neutralized with aqueous ammonia and the resulting precipitate was washed with water to obtain a pasty thallium hydroxide. It was uniformly kneaded together with the above-mentioned $NH_4^+$ form ZSM-11 zeolite in a mortar and the mixture was dried at 110° C. for 14 hours to obtain an $NH_4^+$ form of ZSM-11 zeolite containing $Tl_2O$. Then, this zeolite was subjected to ion-exchange with an aqueous solution containing platinum ammine complex nitrate at 80° C. for 2 hours, and the resulting product was dried at 110° C. for 16 hours, and calcined in air at 530° C. for 4 hours to obtain a catalyst having $Tl_2O$ content of 0.8% and Pt content of 0.01%.

Using this catalyst, a reaction was carried out in the same manner as in Example 1 to obtain the results shown in Table 1.

COMPARATIVE EXAMPLE 1

A catalyst was prepared by calcining the $NH_4^+$ form ZSM-5 synthesized in Example 1 at 530° C. for 4 hours in air.

Using this catalyst, a reaction was carried out in the same manner as in Example 1 to obtain the results shown in Table 1.

COMPARATIVE EXAMPLE 2

A catalyst having Tl content of 3.0% was prepared by calcining the $Tl^+$ form ZSM-5 synthesized in Example 1 at 530° C. for 4 hours in air.

Using this catalyst, a reaction was carried out in the same manner as in Example 1 to obtain the results shown in Table 1.

TABLE 1

| | Catalyst | No. of reaction/ regeneration cycle | Yield (%) Pyridine | Picoline α | β | γ | Total |
|---|---|---|---|---|---|---|---|
| Example 1 | $Tl^+$ form ZSM-5-Pd | 1 | 65 | 6 | 10 | 3 | 84 |
| | | 50 | 61 | 6 | 10 | 3 | 80 |
| Example 2 | $Zn^{++}$ form ZSM-5-Ru | 1 | 55 | 6 | 12 | 5 | 78 |
| | | 50 | 49 | 5 | 13 | 5 | 72 |
| Example 3 | $CD^{++}$ form ZSM-5-Pd | 1 | 43 | 4 | 10 | 6 | 63 |
| | | 50 | 39 | 4 | 11 | 5 | 59 |

TABLE 1-continued

| | Catalyst | No. of reaction/ regeneration cycle | Yield (%) Pyridine | Picoline α | β | γ | Total |
|---|---|---|---|---|---|---|---|
| Example 4 | Pb$^{++}$ form Silicalite (Al$_2$O$_3$ binder-molded)-Pt | 1 | 62 | 5 | 9 | 3 | 79 |
| | | 50 | 57 | 5 | 10 | 4 | 76 |
| Example 5 | Iron silicate/PbO—Pt | 1 | 55 | 7 | 12 | 7 | 81 |
| | | 50 | 51 | 7 | 12 | 7 | 77 |
| Example 6 | Ga silicate/CoO/Kaolin-Pt | 1 | 52 | 5 | 10 | 4 | 73 |
| | | 50 | 47 | 5 | 11 | 4 | 67 |
| Example 7 | Co$^{++}$ form boroaluminosilicate-Rh | 1 | 51 | 6 | 10 | 5 | 72 |
| | | 50 | 46 | 5 | 10 | 5 | 66 |
| Example 8 | H$^+$ form ZSM-11/Tl$_2$O—Pt | 1 | 63 | 6 | 8 | 4 | 82 |
| | | 50 | 60 | 5 | 9 | 5 | 79 |
| Comparative Example 1 | H$^+$ form ZSM-5 | 1 | 42 | 3 | 11 | 5 | 61 |
| | | 30 | 33 | 2 | 10 | 4 | 49 |
| Comparative Example 2 | Tl$^+$ form ZSM-5 | 1 | 63 | 6 | 9 | 3 | 81 |
| | | 30 | 55 | 6 | 10 | 3 | 74 |

What is claimed is:

1. A process for producing pyridine bases which comprises reacting an aliphatic aldehyde of the formula R$^1$CHO wherein R$^1$ is hydrogen, alkyl having 1 to 3 carbon atoms or alkenyl having 2 to 3 carbon atoms and/or a ketone of the formula R$^2$COR$^3$ wherein R$^2$ is methyl or ethyl and R$^3$ is methyl with ammonia in the presence of a catalyst in a gaseous phase, said catalyst comprising a zeolite incorporated with
(a) an element selected from the group consisting of platinum, palladium, rhodium and ruthenium and (b) an element selected from the group consisting of Tl, Pb and Co, and said zeolite having an atomic ratio of Si to at least one element selected from the group consisting of Al, B, Fe and/or Ga of about 12 to about 1,000 and a constraint index of about 0.8 to about 12.

2. A process according to claim 1, wherein the method for incorporation of an element selected from the group consisting of platinum, palladium, rhodium and ruthenium into the zeolite is achieved by subjecting the zeolite to ion-exchange with an ion having said element and/or kneading, impregnating, immersing, precipitating or evaporating to dryness the zeolite together with a compound of said element.

3. A process according to claim 1, wherein said incorporation of at least one element selected from the group consisting of Zn, Cd, Tl, Pb and Co into the zeolite is achieved by subjecting the zeolite to ion-exchange with an ion having said element and/or kneading, impregnating, immersing, precipitating or evaporating to dryness the zeolite together with a compound of said element.

4. A process according to claim 2, wherein said ion is an ammine complex ion.

5. A process according to claim 2, wherein said compound is an ammine complex compound.

6. A process according to claim 1 or 3, wherein said element is an element selected from the group consisting of thallium, lead and cobalt.

7. A process according to claim 1, wherein said zeolite has a crystal structure of ZSM-5 or ZSM-11.

* * * * *

UNITED STATES PATENT AND TRADEMARK OFFICE
CERTIFICATE OF CORRECTION

PATENT NO. : 5,237,068
DATED      : Aug. 17, 1993
INVENTOR(S): Shinkichi SHIMIZU et al It is certified that error appears in the above-identified patent and that said Letters Patent is hereby corrected as shown below:

Col. 5, line 56, "For obtaining β-picoline" should read

--For obtaining α-picoline--.

Signed and Sealed this

First Day of October, 1996

Attest:

BRUCE LEHMAN

Attesting Officer

Commissioner of Patents and Trademarks